(12) United States Patent
Panian (10) Patent No.: US 11,890,024 B2
(45) Date of Patent: *Feb. 6, 2024

(54) CATHETER ASSEMBLY FOR BLOOD CLOTS REMOVAL

(71) Applicant: Anoxia Medical Inc., Hayward, CA (US)

(72) Inventor: Justin Panian, San Francisco, CA (US)

(73) Assignee: Anoxia Medical Inc., Hayward, CA (US)

( * ) Notice: Subject to any disclaimer, the term of this patent is extended or adjusted under 35 U.S.C. 154(b) by 385 days.

This patent is subject to a terminal disclaimer.

(21) Appl. No.: 17/384,203

(22) Filed: Jul. 23, 2021

(65) Prior Publication Data

US 2021/0346040 A1  Nov. 11, 2021

Related U.S. Application Data

(63) Continuation of application No. 16/413,935, filed on May 16, 2019, now Pat. No. 11,096,703, which is a continuation-in-part of application No. 15/587,142, filed on May 4, 2017, now abandoned.

(51) Int. Cl.
| | |
|---|---|
| *A61M 25/01* | (2006.01) |
| *A61B 17/22* | (2006.01) |
| *A61M 39/06* | (2006.01) |
| *A61M 25/00* | (2006.01) |
| *A61M 1/00* | (2006.01) |
| *A61B 90/00* | (2016.01) |
| *A61B 17/00* | (2006.01) |

(52) U.S. Cl.
CPC .............. *A61B 17/22* (2013.01); *A61M 1/71* (2021.05); *A61M 25/005* (2013.01); *A61M 25/0012* (2013.01); *A61M 25/0082* (2013.01); *A61M 25/0105* (2013.01); *A61M 39/06* (2013.01); *A61B 2017/00991* (2013.01); *A61B 2017/22079* (2013.01); *A61B 2090/0811* (2016.02); *A61B 2090/3966* (2016.02); *A61B 2217/005* (2013.01); *A61M 1/80* (2021.05); *A61M 2210/0693* (2013.01); *A61M 2210/125* (2013.01); *A61M 2210/127* (2013.01)

(58) Field of Classification Search
CPC ............ A61M 25/0012; A61M 25/005; A61M 25/0082; A61M 25/0105; A61M 25/0051; A61M 25/0052; A61M 25/0053; A61B 17/22; A61B 2090/3966

See application file for complete search history.

(56) References Cited

U.S. PATENT DOCUMENTS

| | | | |
|---|---|---|---|
| 2002/0026145 A1* | 2/2002 | Bagaoisan | A61M 25/0009 606/192 |
| 2018/0056037 A1* | 3/2018 | Shimizu | A61M 25/0052 |
| 2019/0366036 A1* | 12/2019 | Jalgaonkar | A61M 25/0133 |

* cited by examiner

*Primary Examiner* — Katherine H Schwiker
(74) *Attorney, Agent, or Firm* — Raymond Sun (57) ABSTRACT

A medical device comprises a catheter and an aspiration pump. The catheter has a hybrid reinforcement to improve performance characteristics. The aspiration pump is cycled to improve aspiration efficacy.

14 Claims, 8 Drawing Sheets

CATHETER ASSEMBLY FOR BLOOD CLOTS REMOVAL

RELATED CASES

This application is a Continuation-In-Part of U.S. patent application Ser. No. 15/557,142, filed on May 4, 2017.

BACKGROUND OF THE INVENTION

1. Field of the Invention

The present invention relates to methods and devices for removing thromboembolic materials and other tissue from human body.

2. Description of the Prior Art

Endovascular catheters have been commonly used to remove thromboembolic blockages and other tissue from endovascular and non-endovascular locations in the human body. Single-lumen catheters are employed to aspirate a clot from a cerebral vessel, coronary vessels and peripheral vessels. Such procedure in most cases includes placing a distal end/tip of a catheter at the proximal face of the clot and applying vacuum to the clot via a proximal port of the catheter. Fresh and soft clot usually are easily aspirated, while harder, more organized clot tends to clog the catheter. In such cases, the catheter with trapped clot and under suction is removed outside the patient. Then, the removed catheter is cleaned and introduced again to the treatment location to continue the clot removal process if necessary. However, in some cases, the clot is broken up in pieces by mechanical means during catheter removal and multiple introductions, causing a distal embolization and often dangerous clinical complications.

The latest development of aspiration devices has significantly improved recanalization rates. A direct aspiration, the ADAPT technique for stroke thrombectomy, was recently shown to be an effective and rapid way to achieve cerebral revascularization. This technique focuses on engaging and removing a clot without the use of ancillary devices and solely relying on aspiration forces generated by the suction pump through the catheter. While the use of aspiration alone to remove blood clots has significantly improved in the last several years, a single pass/use success rate still remains below 75%. Therefore, there is a need for better aspiration devices which are simple to use, and can quickly and safely remove thromboembolic material.

SUMMARY OF THE DISCLOSURE

There are three approaches to improve efficacy of removing blood clots using aspiration with a single lumen aspiration catheter: use of stronger vacuum pumps to aid in aspiration of the clot through the catheter, use of larger aspiration catheters; and use of aspiration catheters with expandable tips.

Currently used air aspiration pumps are reaching almost an absolute vacuum of approximately 29 in-Hg (>14 psi) while aspirating air from a blood collection container with a maximum liquid negative pressure of around 27.0 in-Hg. Use of liquid pumps may be beneficial and may increase direct blood aspiration to 28+ in-Hg. Another option is to increase the size (e.g., inner lumen) of the aspiration catheters. Increasing the size of the inner lumen of an aspiration catheter while maintaining the same diameter for the outer lumen is challenging because this compromises the required performance characteristics for the catheter, such as, for example, kink resistance. Use of innovative reinforcement may be helpful. Other options include the use a catheter with a larger frontal aperture.

Cerebral vessels have a complex vessel pattern, and extensive catheter manipulations with a larger size catheter when accessing and navigating these vessels may be risky and may cause vessel dissections, perforations and stroke. However, neuro-interventionists would benefit from the availability of catheters that can be easily, quickly and safely delivered through a standard guide catheter, providing a more effective vehicle to aspirate blood clots.

Increasing the inner lumen size of the aspiration catheters is in most cases related to enlarging the outer size of the catheter, and such approach carries challenges to access the treatment sites, potential clinical complications, and longer procedure time. It is especially risky with the continuous exodus of neurosurgeons to the interventional Neuro-Radiology Field whose manual skills are not always sufficient for such tasks. Therefore, use of aspiration catheters which are easier to navigate and locate at the treatment site with an improved reinforcement structure, and/or expandable tips, may present an attractive and desirable clinical alternative to improve blood clot removal.

The present invention provides alternative options to increase efficacy of clot removal by increasing the flow of removed clots. Increasing the flow within the aspiration catheter may be accomplished by enlarging at least partially the aspiration lumen by combining two catheters that are always an integral part of interventional procedures together: the aspiration catheter and a guide catheter or sheath. Merging these two catheters may be accomplished by placing a modified aspiration catheter having a smaller and shorter tubular body within a larger and longer guide catheter, while providing a suitable seal between them for aspiration. Such approach will increase flow within two combined catheters and result in more efficient clot aspiration.

Furthermore, such modified extension catheters comprising a short tube attached to a long pushing/pulling wire may have a larger inner lumen compared with longer conventional aspiration catheters. Thus, such short extension catheters may considerably minimize challenges with navigating aspiration catheters to the treatment sites and maneuvering the catheter during clot-removal.

Additionally, it is also beneficial to provide a larger catheter opening surface on the distal end of the extension catheter. For example, instead of using a conventional circular aperture on the distal end of the aspiration catheter, applying an oval or angulated aperture may improve clot removal. A larger opening lumen of the aspiration catheter may also be achieved by using an expandable tip on the distal end of aspiration catheter. Such expandable tip may be suitable not only when implemented with an extension catheter of the present invention but also with any conventional aspiration catheter currently in clinical use.

The present invention comprises a coaxial catheter assembly including a guide catheter or sheath, and a shorter aspiration catheter or an extension catheter for use to remove thromboembolic material from the human body. The treatment site may include but is not limited to endovascular locations such as coronary circulation, cerebral and other peripheral circulation, but may also include non-endovascular locations. The guide catheter is delivered into the body through a standard introducer with a hemostatic valve utilizing a conventional 0.025"-0.038" guidewire. After the guide catheter or sheath is placed inside the body, a 0.025"-0.038" guidewire is removed and a smaller guidewire in sizes between 0.008"-0.018" is placed at the treatment location. All these activities are performed under fluoroscopy or using other imaging techniques. Once the smaller guidewire is positioned at or through the treatment site, the extension catheter is introduced over a smaller guidewire into the guide catheter or sheath to the proximal part of the clot or other tissue to be removed. The distal part of the extension catheter is placed outside the guide catheter while the proximal part of the extension catheter remains inside the guide catheter. The clot/tissue removal process begins when a suction pump attached to the proximal end of the guide catheter is activated. Upon activation of suction, a seal between the guide catheter and the extension catheter is activated and blood clots are aspirated from the treatment site outside the body.

In one aspect of the present invention, a catheter assembly for blood clots and other tissue removal comprises a guide catheter having a distal end, a proximal end and a lumen extending longitudinally, and an extension catheter positioned at least partway inside the guide catheter. The extension catheter includes a distal tubular portion or member and has an open distal end and an open proximal end. The proximal open end of the extension catheter is attached to a pushing/pulling wire that is extended along the inner lumen of the guide catheter and outside the proximal end of the guide catheter. The extension catheter may freely move inside and outside of the guide catheter.

In one embodiment, the extension catheter has a variable flexibility, being more flexible on the distal end and less flexible on the proximal end.

In another embodiment, the pushing wire is further attached to the distal end of the extension catheter. The pushing wire may be located in one of the following locations: extended along the main lumen of the extension catheter, placed in a separate lumen within the extension catheter, or partially located in both.

The distal tubular portion/member of the extension catheter is configured to be extended beyond the distal end of the guide catheter while the proximal portion of the tubular member of the extension catheter remains within the lumen of the guide catheter. The extension catheter portion that remains inside the guide catheter includes at least partially the tubular member and the attached pushing wire.

The inner lumen of the guide catheter and inner lumen of the extension catheter are aligned accordingly to allow contrast injection and aspiration of blood clots and other tissue.

In yet another embodiment, the tubular portion/member of the extension catheter may have one of the following openings on the distal and proximal ends, including but not limited to, circular, oval, irregular or any other shape.

In another embodiment, the extension catheter is adopted for insertion into the proximal end of the guide catheter, can be moved along the entire length of the guide catheter, and may also be at least partially positioned outside of the distal end of the guide catheter.

The guide catheter and the extension catheter may be provided in separate packages, or in one package with two separate devices.

In yet another embodiment, the inner diameter of the guide catheter is at least 0.002" larger than the outer diameter of the extension catheter.

In another embodiment, the extension catheter has a hydrophilic coating on the outside surface, or a hydrophobic coating on the outside surface, or a combination of both coatings.

In yet another embodiment, a conventional metal pushing/pulling wire is attached to the distal end of the extension catheter, and such wire may have a variety of sizes and configurations, including circular, oval, square, flat, irregular and a combination thereof.

In another embodiment, the extension catheter is at least partially made of one of the following materials, including but not limited to polymers, reinforced polymers, metals, or a combination thereof.

In yet another embodiment, an aspiration feature is attached to the proximal end of the guide catheter and may include any suitable vacuum device or machinery attached to the proximal end of the guide catheter, including a hospital line suction, a reusable pump, a disposable pump, syringes and a combination thereof.

In another embodiment, a seal between the guide catheter and the extension catheter is achieved by using a soft tip mounted on the distal end of the guide catheter. When the guide catheter/extension catheter is under vacuum, the soft tip collapses and squeezes around the extension catheter, providing a suitable seal for aspiration of blood clots.

In yet another embodiment, a hydrophilic coating is applied on the external surface of the extension catheter to further reduce friction between the extension catheter and the guide catheter and to provide a seal between the guide catheter and the extension catheter.

In another embodiment, a hydrophobic coating is applied on the external surface of the extension catheter to further reduce friction between the extension catheter and the guide catheter and to provide a seal between the guide catheter and the extension catheter.

In another aspect of the present invention, a catheter assembly for blood clots and other tissue removal comprises a guide catheter with at least one longitudinal lumen, and an extension catheter having a tubular member with a pushing wire attached and positioned through the guide catheter. The distal end of the tubular member is located outside the guide catheter and the proximal end of the tubular member is located inside the guide catheter. A suction source is attached to the proximal end of the guide catheter and provides more than 20 in-Hg aspiration pressure at the distal end of the extension catheter. The extension catheter may freely move within the guide catheter when aspiration is applied.

In another embodiment, the outer surface of the extension catheter has a texture to further enable and support the seal space between the outer catheter and the guide catheter during aspiration. Such textured surface may be coated with a hydrophilic coating or hydrophobic coating, or both. The surface texture may comprise a small local deviation of a surface from the perfectly flat or smooth surface, and include surface roughness or waviness.

In another aspect, a catheter assembly for blood clots and other tissue removal comprises a guide catheter and an extension catheter. The guide catheter has a distal end, a proximal end and at least one lumen extending longitudinally. A soft tip is provided on the distal end of the guide catheter. The extension catheter is positioned through and distally to the guide catheter such that the proximal end of the extension catheter is located inside the guide catheter. A suction source is attached to the proximal end of the guide catheter and provides aspiration pressure along the guide catheter and the extension catheter. During aspiration, a soft tip of the distal end of the guide catheter collapses around, embraces or surrounds the extension catheter, providing a sufficient seal for aspiration of clots.

In another aspect of the present invention, the presence of blood, saline or contrast may surround the area of the soft tip and further provide a seal between the extension catheter and the guide catheter when under aspiration.

In another aspect of the present invention, a catheter assembly for blood clots and tissue removal comprises a guide catheter having at least one lumen extending longitudinally, and an extension catheter positioned through and distally to the guide catheter. The distal end of the extension catheter is outside the guide catheter and the proximal end of the extension catheter remains inside the guide catheter. There is a seal between the extension catheter and guide catheter. A suction source attached to the proximal end of the guide catheter provides aspiration pressure along the guide catheter and the extension catheter. The inner lumen along the extension catheter is smaller than the inner lumen within the guide catheter to facilitate the flow of clots.

In yet another aspect of the present invention, a catheter assembly for blood clots and tissue removal comprises a guide catheter having an inner lumen extending longitudinally and an extension catheter having an inner lumen extending longitudinally and at least partially placed through the guide catheter. The catheter assembly further includes means for sealing space between the extension catheter and the guide catheter. The inner lumen along the guide catheter is larger than the inner lumen along the extension catheter to increase the flow of blood clots.

In another aspect of the present invention, a catheter assembly for blood clots and tissue removal comprises a guide catheter having an inner lumen extending longitudinally, an extension catheter having a tubular portion, and a pushing wire attached to the proximal end of the tubular portion. An expandable tip is located on the distal end of the tubular portion, and the tubular portion of the extension catheter is positioned at least partially inside of the guide catheter.

In one embodiment, the expandable tip comprises a tubular braid having a proximal end attached to the distal end of the tubular portion of the extension catheter. Such tubular braid is coated with a silicone to secure a shielded tubular configuration.

In another embodiment, the catheter assembly further includes means for sealing the space between the tubular member of the extension catheter and the guide catheter.

In yet another embodiment, the distal expandable tip opens to a larger size upon release from the guide catheter than its size inside the guiding catheter.

In another embodiment, the tubular member of the extension catheter is configured to be pushed through and out of the guide catheter and retrieved back into the guide catheter using the pushing wire.

In yet another embodiment the pushing/pulling wire may be attached to the tubular braid.

In another embodiment, the tubular braid is configured to have a pre-set expanded shape when released from the guide catheter and such pre-set expanded shape may include the following configurations: tubular, funneled, siphoned, coned, tapered or other similar shape that provides at least partial tip expansion of the tubular braid when pushed outside the guide catheter.

In another aspect of the present invention, a method for removing blood clots from a treatment location in patient comprises placing a guide catheter inside the patient, positioning a guide wire through the guide catheter at the treatment location, and introducing an extension catheter over the guide wire into the guide catheter to the treatment location. The extension catheter comprises a distal tubular portion/member, and a wire attached to the proximal end of the distal tubular portion/member, wherein the distal end of the extension catheter is partially extended beyond the guide catheter while the proximal end of extension catheter is located inside the guide catheter. Finally, blood clots are aspirated outside the patient using suction attached to the proximal end of the guide catheter.

In another embodiment, the extension catheter may be repositioned during the removal of blood clots.

In yet another embodiment, repositioning of the extension catheter is performed during one of the following steps: when the extension catheter and guide catheter are under vacuum, under no vacuum, and during both steps.

In another embodiment, placing the guide catheter includes placing a sheath.

In yet another embodiment, there is a seal between the guide catheter and the extension catheter to secure the suction of blood clots from the treatment location through the extension catheter, through the guide catheter and outside the patient.

In another embodiment, a seal between the extension catheter and the guide catheter is achieved by a soft tip on the distal end of the guide catheter, by hydrophilic coating of the extension catheter, by hydrophobic coating of the extension catheter, or by a combination thereof. In addition, patient blood, contrast and saline may also aid in securing the seal.

In yet another embodiment, the guidewire is placed beyond blood clots and remains in place during the removal of blood clots.

In another embodiment, the guidewire is removed from the patient after placement of the extension catheter at the treatment site and during clots removal.

In yet another embodiment, the extension catheter and guide catheter are removed from the treatment location when the extension catheter gets clogged.

In yet another embodiment, cleaning the extension catheter from clots is performed outside the patient, and the extension catheter may be introduced again to the treatment area to continue the removal of blood clots.

In another embodiment, the guide catheter together with the extension catheter are removed outside the patient, cleaned and reintroduced again to continue clot removal.

In another aspect of the present invention, a method for removing blood clots from a treatment location in patient comprises placing a guide catheter inside the patient, positioning a guide wire through the guide catheter at the treatment location, and introducing an extension catheter over the guide wire into the guide catheter to the treatment location. The extension catheter comprises a distal tubular portion/member having a distal end and a proximal end, and a pushing/pulling wire attached to the proximal end. The distal end of the extension catheter is partially extended beyond the guide catheter while the proximal end of extension catheter is located inside the guide catheter. Finally, blood clots are aspirated outside the patient using suction attached to the proximal end of the guide catheter, and wherein the clot flow within the distal end of the extension catheter is slower than within the guide catheter.

In another aspect of the present invention, a method for removing blood clots and other tissue from patient comprises placing a guide catheter having a soft tip inside the patient, positioning a guide wire through the guide catheter at the treatment location, introducing an extension catheter with an expandable tip over the guide wire into the guide catheter to the treatment location, and aspirating blood clots outside the patient using suction attached to the proximal end of the guide catheter.

In another embodiment, the distal expandable tip opens to a larger inner lumen upon release from the guide catheter than inside the guiding catheter, so as to increase the efficacy of the removal of clots.

In another embodiment, the tubular member of the extension catheter is configured to be pushed through and out of the guide catheter. and retrieved back into the guide catheter using the pushing wire before blood clots removal, during blood clot removal, and during a combination of both.

In yet another embodiment, the tubular braid is suitable to assume a pre-set expanded shape having a larger distal inner lumen than the proximal lumen when pushed outside of the guide catheter.

In another aspect of the present invention, a device comprising an aspiration catheter and a liquid cycling aspiration pump are provided to increase efficacy of clot removal.

In yet another aspect of the present invention, an endovascular catheter includes an elongate flexible catheter body having a proximal end, a distal end and a side wall defining a central lumen. The side wall includes a tubular inner liner and a hybrid reinforcement that includes a helical coil and a braid. An outer jacket encloses the hybrid reinforcement and is formed from a plurality of tubular segments positioned end to end, coaxially along the hybrid reinforcement.

In yet another aspect of the present invention, the flexural load profile along the length of the catheter is configured to provide enhanced distal flexibility, overall pushability and back up support while minimizing the overall wall thickness of the catheter having a wall thickness ratio with the catheter inner diameter to catheter outer diameter that is higher than 0.80.

In accordance with another aspect of the present invention, the inner liner may be formed by dip coating with a removable mandrel or it may be made from PTFE.

The following terms: "aspiration", "vacuum" and "suction" are commonly used in this application, and all are related to using negative pressure that generally pertains to the movement of blood clots and other tissue caused by negative pressure.

The following terms endovascular catheter, aspiration catheter and catheter have the same functional meaning, and all may be related to the removal of plaque, tissue, blood clots, blood and other liquids from the human body, as well as being used to deliver medications, implants, therapeutic agents and other matters.

As used herein, "treatment site" refers to any location in the body that has been or to be treated by methods or devices of the present invention. Although "treatment site" often refers to an endovascular area including arteries and veins, the treatment site is not limited to endovascular tissue or blood clots. The treatment site may include tissues and blood clots associated with outside of endovascular location, including but not limited to bodily lumens, organs, ducts or localized tumors.

The treatment sites of the present invention involve blood vessels in the patient's vasculature, including veins, arteries, aorta, heart valves and particularly including cerebral, coronary and peripheral arteries, as well as previously implanted grafts, shunts, fistulas and the like. In alternative embodiments, methods and devices to remove blood clots and other tissue described herein may also be applied, but are not limited to, the biliary duct, head, nerves, glands, and the like.

The scope of the present invention is best defined by drawings, descriptions below and the appended claims. In certain instances, descriptions of vacuum physics, well-known devices, compositions, components, mechanisms and methods are omitted so as to not obscure the description of the present invention with unnecessary details.

Some theoretical considerations have been introduced in the present invention for assessing and exploring how these therapeutic methods are effective. These considerations have been provided only for presenting an understanding of the invention only and have no relevance to or bearing on the claims.

DETAILED DESCRIPTION OF THE PREFERRED EMBODIMENTS

Figure 1:
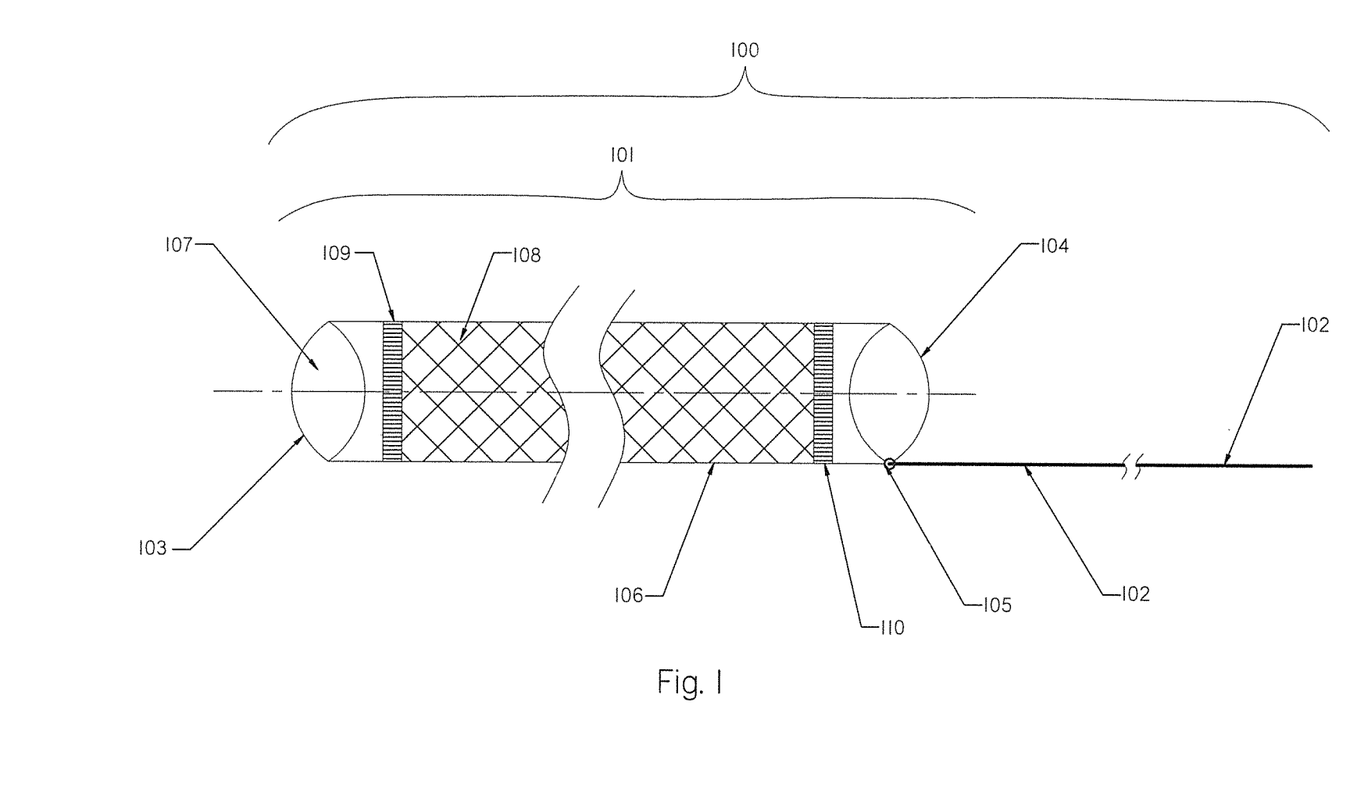
FIG. 1 illustrates an extension catheter according to one embodiment of the present invention.

FIG. 1 illustrates an extension catheter 100 that includes a tubular portion 101 and a pushing/pulling wire 102. The tubular portion 101 has a distal end 103 and a proximal end 104. The wire 102 is attached to the proximal end 104 of the tubular portion 101 at a connection point 105. The extension catheter 100 has an outer lumen 106 and an inner lumen 107. The tubular portion 101 may also include a reinforced wall 108. One radiopaque marker 109 is located on the distal end 103 of the tubular portion 101, and another radiopaque marker 110 is located on the proximal end 104 of the tubular portion 101. The tubular portion 101 of the extension catheter 100 may be 2-100 cm long, while the attached pushing/pulling wire 102 may have any size and length suitable for interventional procedures.

The tubular portion 101 may be constructed from any suitable biocompatible plastics and elastomers used in medical devices exhibiting the following characteristics: flexibility, durability, softness, and easily conformable to the shape of the treatment and to minimize risk of harm and trauma.

The tubular portion 101 may also include an inner liner (not shown). The inner liner may be of a polymeric lubricious composition including but not limited to polytetrafluoroethylene (TFE) polymer to reduce friction. The reinforcement 108 may include but is not limited to braid, coils, knit and combinations thereof. The materials of choice can be stainless steel, polymers and super-elastic alloys such as Nitinol.

The reinforcement 108 may be partially constructed of polymeric fibers or carbon fibers either replacing a portion of the metallic ribbons/wires or polymeric materials or placed in conjunction with a ribbon or wires in the braid. Other metals (e.g., noble metals such as members of the platinum group or gold) may be used in the braid itself in much the same way to impart radiopacity to the braid. To tailor the stiffness of the braid, the braid may first be wound and portions of the ribbon then removed. Also, the reinforcement 108 may be discontinuous leaving polymer alone without reinforcement.

Ribbons or wires making up the braid and coils can also contain a minor amount of other materials. Fibrous materials, both synthetic and natural, may also be used. In certain applications, particularly smaller diameter catheter sections, more malleable metals and alloys (e.g., bold, platinum, palladium, rhodium, etc.) may be used. A platinum alloy with a few percent of tungsten is sometimes preferred partially because of its radiopacity. Suitable nonmetallic ribbons or wires include materials such as those made of polyaramides (Kevlar), polyethylene terephthalate (Dacron), or carbon fibers.

The pushing/pulling wire 102 attached to the tubular portion 101 of the extension catheter 100 may have variety of configurations including but not limited to circular, oval, square, flat and combinations thereof. The wire 102 may be made with any suitable metal, preferably Nitinol, and may have a variety of tapered section(s) to provide a proper flexibility and ability to pull and push the tubular portion 101 back and forth within the body or other catheters.

Figure 2:
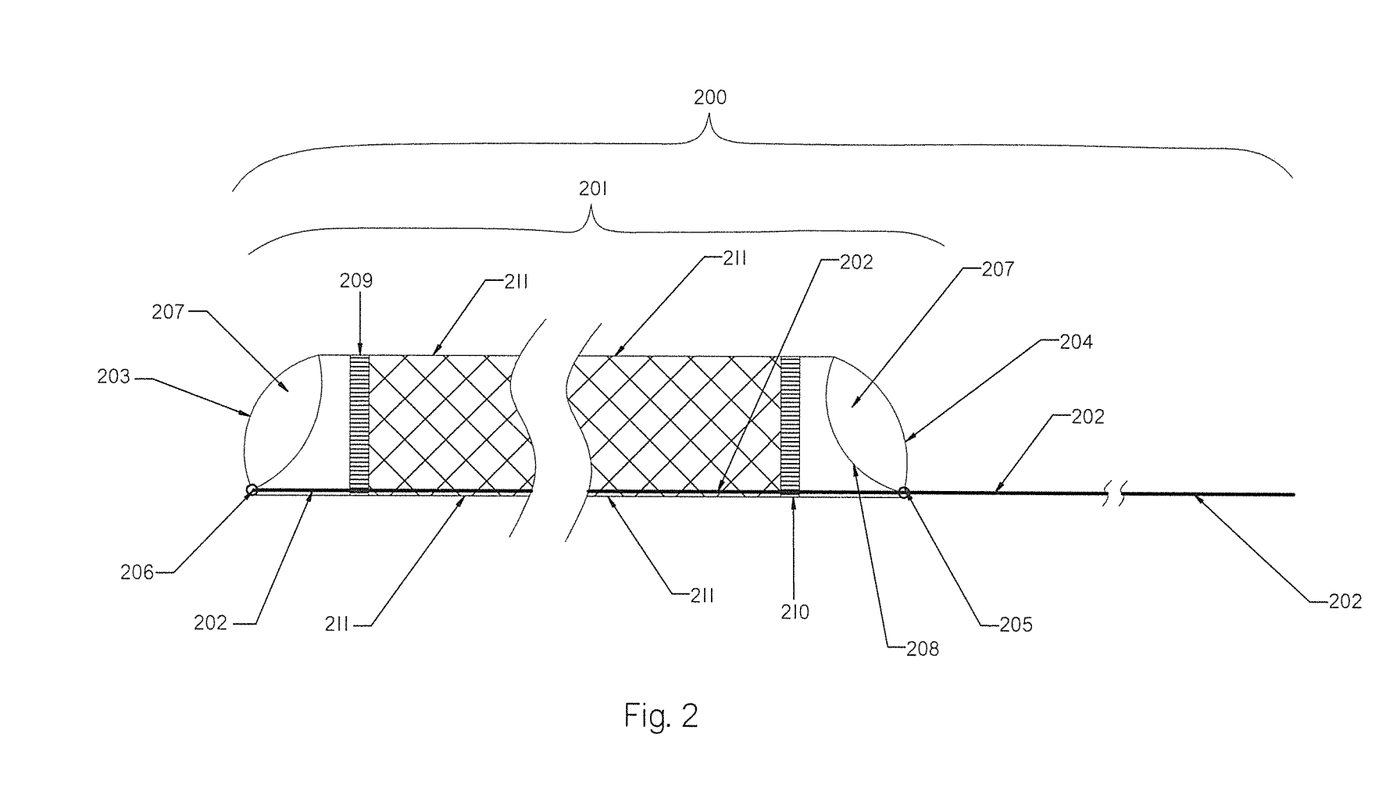
FIG. 2 illustrates an extension catheter according to another embodiment of the present invention.

FIG. 2 shows an alternative configuration for the extension catheter 200. The extension catheter 200 includes the tubular portion 201 and the pushing/pulling wire 202. The tubular portion 201 has a distal end 203 and a proximal end 204. The wire 202 is connected to the proximal end 204 of the tubular portion 201 at a connection point 205 and also is attached to the distal end 203 of the tubular portion 201 at another connection point 206. Such connection of the wire 202 to the distal end 206 and the proximal end 205 of the tubular portion 201 provides an additional internal reinforcement within the tubular portion 201, and provides better pushability of the tubular portion 201 when the extension catheter 200 is introduced into another catheter or navigated inside the body. The extension catheter 200 has an outer lumen 208 and an inner lumen 207. One radiopaque marker 209 is located on the distal end 203 of the tubular portion 201, and another radiopaque marker 210 is located on the proximal end 204 of the tubular portion 201.

The distal end 203 of the tubular portion 201 and the proximal end 204 of the tubular portion 201 may have one of the following openings, including but not limited to circular, oval, elliptical, angulated, irregular shape or combinations thereof. A largest possible aperture or enlargement of the distal end 203 of the tubular portion 201 and/or on the proximal end 204 of the tubular portion 201 will provide higher suction efficacy and better ability to remove blood clots and other tissue.

Coating of the external surface 211 of the tubular portion 201 of the extension catheter 200 may also be beneficial to reduce the friction of the extension catheter 200 but also to facilitate a seal between the tubular portion 201 of the extension catheter 200 and a guide catheter (not shown).

There are two most common coatings that may be used on the surface of the tubular portion 201 of the extension catheter 200: hydrophobic coating and hydrophilic coating. Hydrophobic coatings offer coefficients of friction in the range of approximately 0.15 to 0.3. In contrast, hydrophilic coatings are much more lubricious and have coefficients of friction in the range of 0.005 to 0.2. Hydrophilic coatings, by their nature, must be wet in order to exhibit lubricity, while low friction hydrophobic coatings do not need to be wet. In most cases, a dry hydrophobic coating is more lubricious than a dry hydrophilic coating.

A primary purpose of hydrophobic coatings such as polytetrafluoroethylene or polyxylylene is to act as a barrier against liquids. If a device must be sealed so that moisture, contrast, saline, blood do not get inside or between, one of these hydrophobic coatings will work well to prevent liquids from or on the device's surface and act as a sealant over areas where liquid can penetrate.

Hydrophilic coatings imbibe water and most of them are in fact comprised of more than 90% water when wet. However, most medical hydrophilic coatings rely on primer coats or base coats for adhesion to a surface, and these primers tend to be relatively hydrophobic, which could cause them to act as liquid barriers and serve a seal between outer surface of the tubular portion 201 of the extension catheter 200 and another device.

Given the differences in functions, applications for hydrophobic and hydrophilic coatings are different, and some applications overlap. The present invention may be one of the examples where both coatings may be advantageous.

Figure 3:
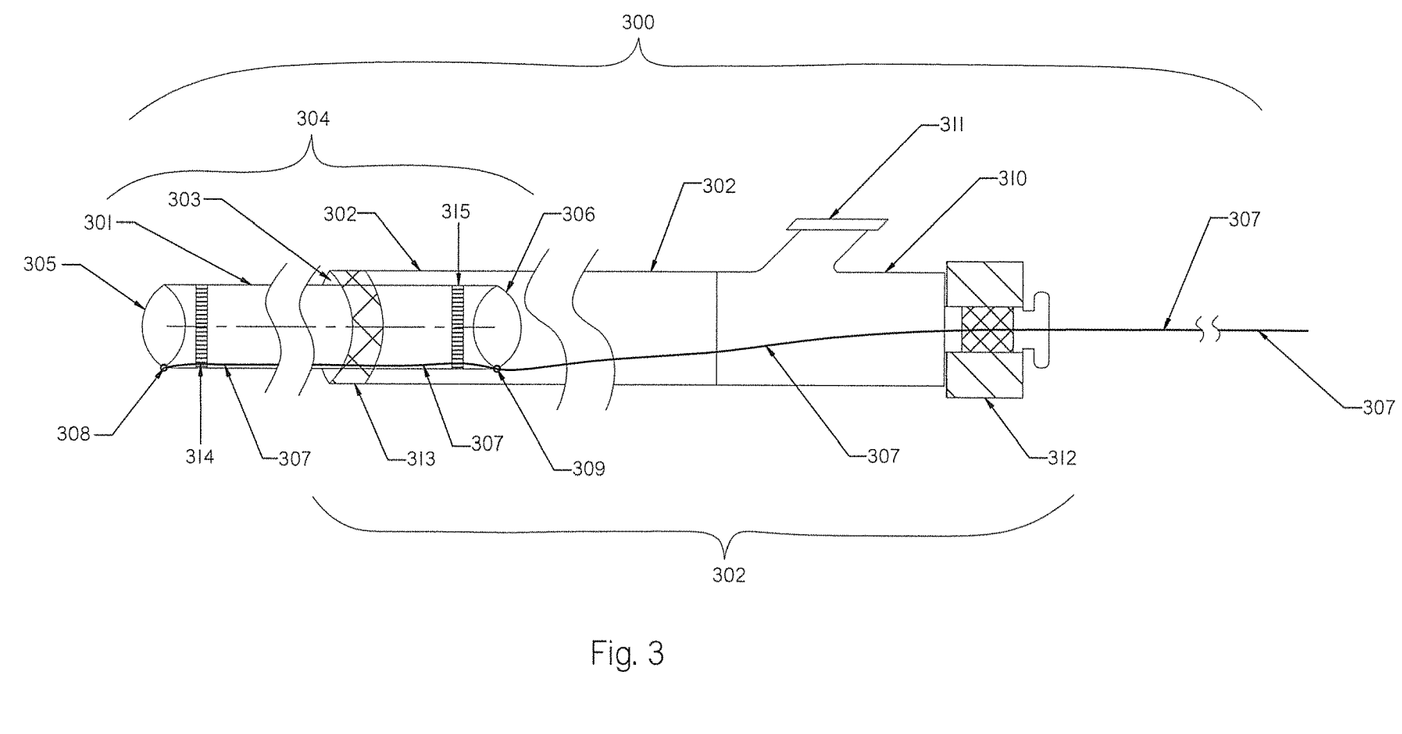
FIG. 3 is a cross-sectional view of a catheter assembly for removal of clots incorporating the extension catheter of FIG. 1.

FIG. 3 shows a cross sectional view of a catheter assembly 300 for removal of clots and other tissue. The catheter assembly 300 comprises an extension catheter 301, a guide catheter 302 and a seal 303. The extension catheter 301 can be the same as the extension catheter 101 of FIG. 1, and is introduced inside the guide catheter 302 through the Touhy Borst 312. The extension catheter 301 comprises a tubular portion 304 having a distal end 305 and proximal end 306. The pushing/pulling wire 307 is attached to the distal end 305 of the tubular member 304 at the attachment area 308, and in this specific embodiment the wire 307 is attached to the proximal end 306 of the tubular member 304 at the attachment area 309. The manner in which the wire 307 is attached to the tubular member 304 improves pushability of the tubular member 304 when introduced into the guide catheter 302, and any other procedural manipulations to and at the treatment site. The distal end 305 of the tubular member 304 is positioned outside the guide catheter 302 while the proximal end 306 of the tubular member 306 is positioned inside the guide catheter 302. The guide catheter 302 comprises a soft tip 313 located on its distal end, and a Y-connector 310 has an outlet arm 311 that functions for suction attachment and the Touhy Borst 312.

The soft tip 313 provides a sealing feature, which under suction from within the guide catheter 302 when suction is applied at the suction port 311 folds around the tubular member 304 (not shown) and secures closure around the guide catheter 302, thus creating vacuum along the tubular portion 304 of the extension catheter 301 and the guide catheter 302. The seal area 303 is configured to allow a free movement of the tubular portion 304 of the extension catheter 301 within the guide catheter 302. One radiopaque marker 314 is located on the distal end 305 of the tubular portion 304 and another radiopaque marker 315 is located on the proximal end 306 of the tubular portion 304.

In the spirit of this invention, the tubular portion 304 of the extension catheter 301 is shorter than the length of the guide catheter 302. The length of the tubular member 304 may be within 2-100 cm long, preferably 15-30 cm long.

Other options to seal the space between the tubular portion 304 of the extension catheter 302 and the guide catheter 302 may include additional member(s) either provided on the outer surface of the tubular portion 304, or within the lumen of the guide catheter 302, or both. Although the seal options have been described above with respect to certain embodiments, it will be appreciated that various changes, modifications and alterations may be made to such above-described seal embodiments without departing from the spirit and scope of the present invention.

Figures 4, 7A:
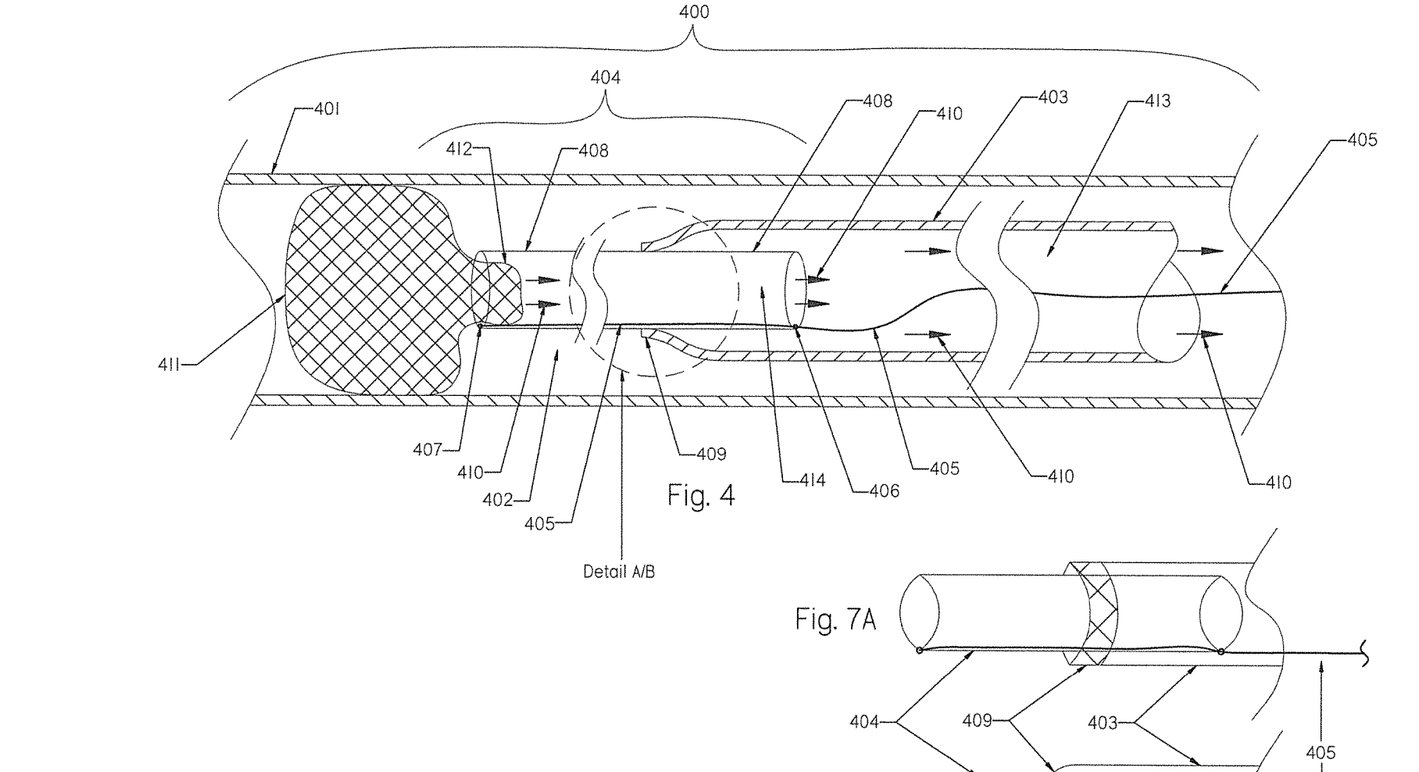
FIG. 4 is an enlarged sectional view of the distal portion of a guide catheter and the extension catheter of FIG. 1.
FIG. 7A is an enlarged sectional view of one embodiment of the area A/B in FIG. 4.

FIG. 4 shows the catheter assembly 400 with an enlarged distal view inside the blood vessel 401. The catheter assembly 400 comprises an extension catheter 402 can be the same as the extension catheter 101 of FIG. 1. The extension catheter 402 is positioned within the distal end of the guide catheter 403. The extension catheter 402 comprises a tubular member 404 and a pushing/pulling wire 405 attached to the tubular member 404 at a proximal attachment area 406 and a distal attachment area 407. A lubricious coating 408 is formed on the outer surface of the tubular member 404. Such coating facilitates movement of the tubular member 404 within the guide catheter 403 and outside of the guide catheter 403 when within the vessel 401. The guide catheter 403 has a soft tip 409 on its distal end which provides a less traumatic interface against vessels and other tissue during introduction of the guide catheter into the body. During the placement of the catheter assembly 400 at the treatment side, when there is no aspiration applied, the soft tip 409 is in an "open" position, as shown in FIG. 7A.

When aspiration is applied at the proximal end of the guide catheter 403 (at the port 311 as shown in FIG. 3), the aspiration is applied to all inner lumens of the catheter assembly 400 along the guide catheter 403 and the tubular portion 404 of the extension catheter 401, as shown by arrows 410. Aspiration from within the catheter assembly 400 affects the clot 411 surrounding the distal end of the tubular portion 404. Under aspiration from within the catheter assembly 400, the clot 411 begins entering the distal end of the tubular portion 404 of the extension catheter 402 as shown by arrows 410.

Figure 7B:
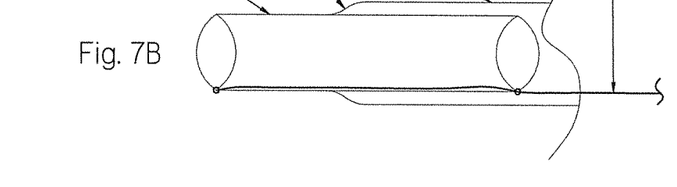
FIG. 7B is an enlarged sectional view of another embodiment the area A/B in FIG. 4.

Once aspiration is applied to the proximal end of the guide catheter 403, the clot 411 starts flowing into the distal end of the tubular portion 404 as shown by the arrows 410, and creates suction flow resistance. After blood clot(s) 411/412 enters the tubular portion 404 of the extension catheter 401, vacuum pressure increases. The soft tip 409 folds around the tubular portion 404 of the extension catheter 402 and begins acting like a seal, as shown in FIG. 7B. With higher aspiration pressure within the catheter assembly 400, a better-yielded seal is produced by the soft tip 409 against or around the guide catheter 403. Also, a blood clot within the seal area (not shown) may aid in providing a better seal.

In addition, the catheter assembly 400 has a unique configuration for the inner aspiration lumens, with a larger inner lumen 413 within the guide catheter 403 than the inner lumen 414 within the tubular portion 404 of the extension catheter 402. This unique configuration increases the flow of aspirated clots and improves the efficacy of clot removal.

Figure 5A:
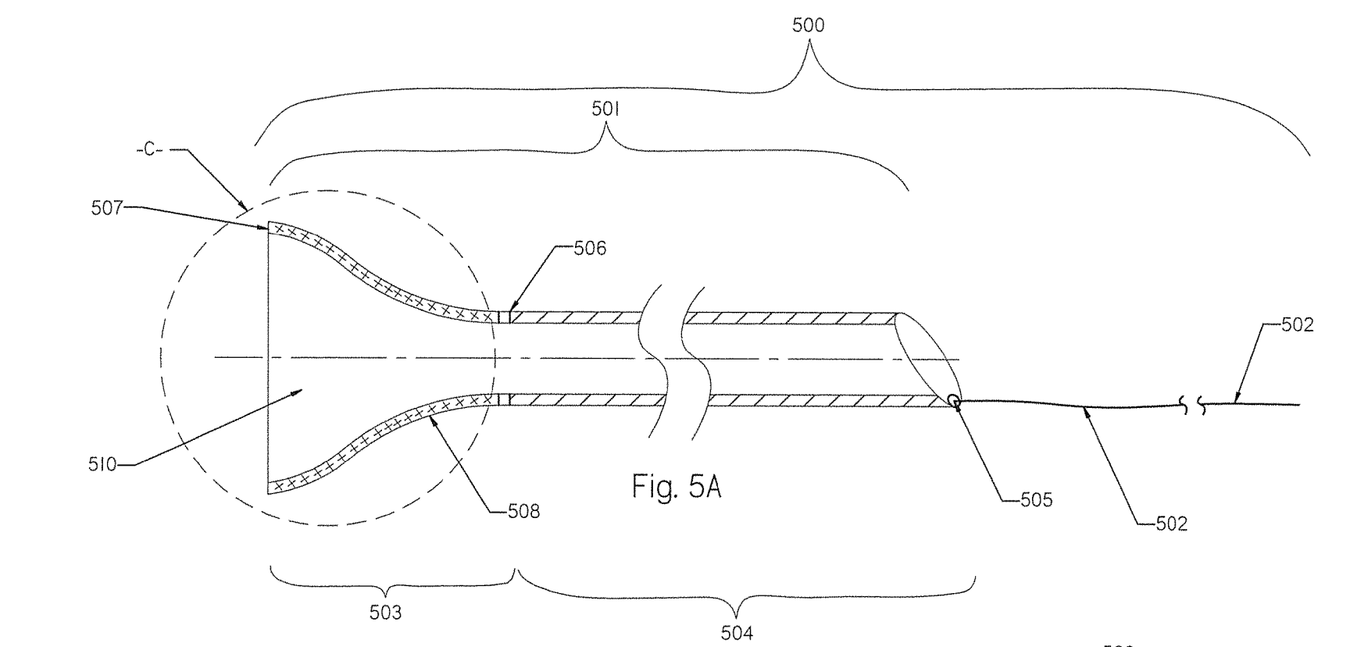
FIG. 5A illustrates another embodiment of the extension catheter with an expandable tip.

FIG. 5A shows an extension catheter 500 according to another embodiment, where the extension catheter 500 comprises a tubular portion 501 and a pushing wire 502. The tubular portion 501 has an expandable tip 503 attached to the main body 504. The pushing wire 502 is attached to the main body 504 of the tubular portion 501 at an attachment area 505. The expandable tip 503 is located on the distal end of the tubular portion 501 and is attached to the tubular portion 501 at an attachment area 506. The expandable tip 503 has a funneled or conical configuration with the very distal end 507 having a larger inner and outer dimension than the proximal end of the expandable tip 503. The expandable tip 503 is shown in an expanded configuration in FIGS. 5A and 5B.

Figure 5B:
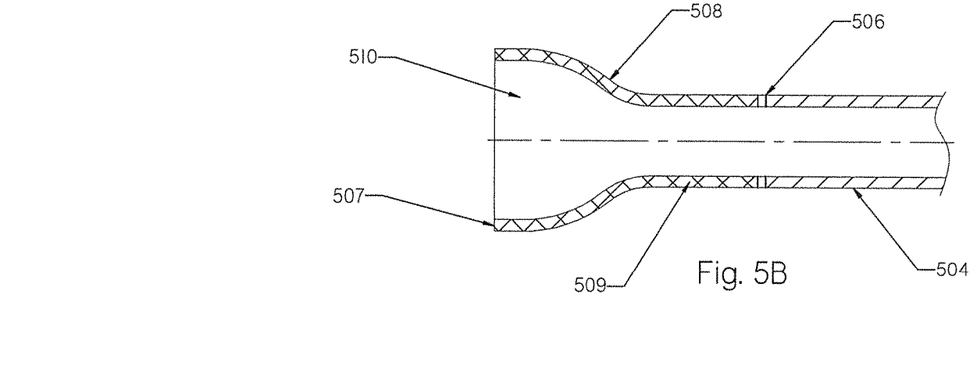
FIG. 5B is an enlarged sectional view of the area C in FIG. 5A.

The expandable tip 503 can be made of a tubular braid 508, is coated and has its complete surface covered with silicone 509, as shown in FIG. 5B. The importance of the expandable tip 503 is the fact that the very distal end 507 has an aperture 510 that has a larger diameter than the diameter of the main body 504. Such larger aperture on the distal end 507 of the tubular member 501 significantly improves the efficacy of blood clot removal.

The space or voids within the braid 508 are filled up and covered with silicone 509, thus creating a shield that prevents penetration and suction of blood clots through the outer surface of the expandable tip 503. Therefore, it guarantees that the maximum vacuum pressure can be applied at the aperture 510.

The tubular braid 508 may be made of a plurality of wires having sizes between 0.0005-0.0030 inches and the same or different inner/outer dimensions, and constructed of wire strands made of metals, alloys, polymers, Nitinol, cobalt-chromium alloys, Platinum, Platinum-Iridium alloys, polymers or combinations thereof. The wire strands may be formed into a tubular circular shape, tubular oval shape or any suitable shapes, and may be made using (but not limited to) circular wires, oval wires, flat wires and combinations thereof.

The angle of the tubular braid 508 (i.e., angle between two crossing filaments of the braid—not shown) plays an important role of easing the expanding and collapsing braid. An easier-collapsing braid requires less force for pushing the braid through other restrictive tubes when in the collapsed configuration; for example, pushing through the guiding catheter. A small braid angle of less than 30 degrees in the collapsed configuration and less than 70 degrees in the expanded configuration will be more amenable and would create less friction during introduction and manipulations within and outside of the guide catheter.

The radial size of the overall braid 508 in the expanded configuration may have dimensions in any range between 0.5 mm-50 mm to assure proper fit into the treatment area. The braid 508 of the expandable tip may have between 8 and 144 strands, and a variety of wire configurations including, but not limited, to: one wire on one wire (1/1); one wire on two wires 1/2); two wires on two wires (2/2); two wires on one wire (2/1) and other suitable combinations.

Silicone or silicone rubbers are synthetic polymers containing silicon together with carbon, hydrogen, oxygen, and are commonly used in medical devices and implants. One of the most unique mechanical properties of silicone rubbers are excellent elongation of 1000% or more, flexibility and a durometer range of 5 to 80 Shore A. Such elongation and durometer ranges will provide the braid 508 with a shield in the expanded and collapsed configurations. It is important to mention that softer forms of silicone have the ability to retain their softness indefinitely.

The most common assembly methods for joining silicone components include insert molding and bonding. While insert molding process involves injection molding around an existing part, bonding normally entails joining silicone components with other polymers with adhesives. In the present invention, the silicone coat 509 is preferably applied on braid 508 and within the braid 508 strands by dipping. Other silicone covering methods may include but are not limited to tipping and cuffing.

Figure 6A:
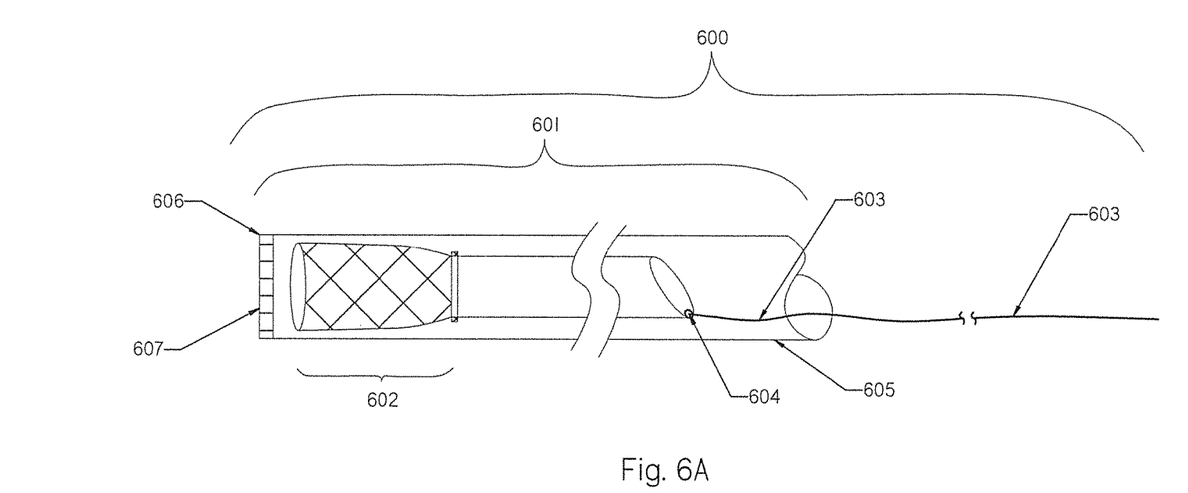
FIG. 6A illustrates the expandable tip of the tubular member of FIG. 5A in a compressed configuration inside the distal end of the guiding catheter.

FIG. 6A shows an extension catheter 600 having a tubular member 601 comprising an expandable tip 602 connected to a pushing wire 603 at a connection area 604. The extension catheter 600 is shown inside the guiding catheter 605, and the extension catheter 600 can be the same as the extension catheter 201 in FIG. 2. A soft tip 606 is located on the distal end 607 of the guiding catheter 605. The tubular member 601 is shown within the guiding catheter 605 before deployment to the treatment site. The expandable tip 602 of the tubular member 601 is in a compressed configuration and exhibits a tubular shape. Once the expandable tip 602 is pushed distally using the pusher wire 603 outside of the guiding catheter 605 and leaves the distal end 607, the expandable tip 602 will assume its expanded configuration 608 as shown in FIG. 6B.

Figure 6B:
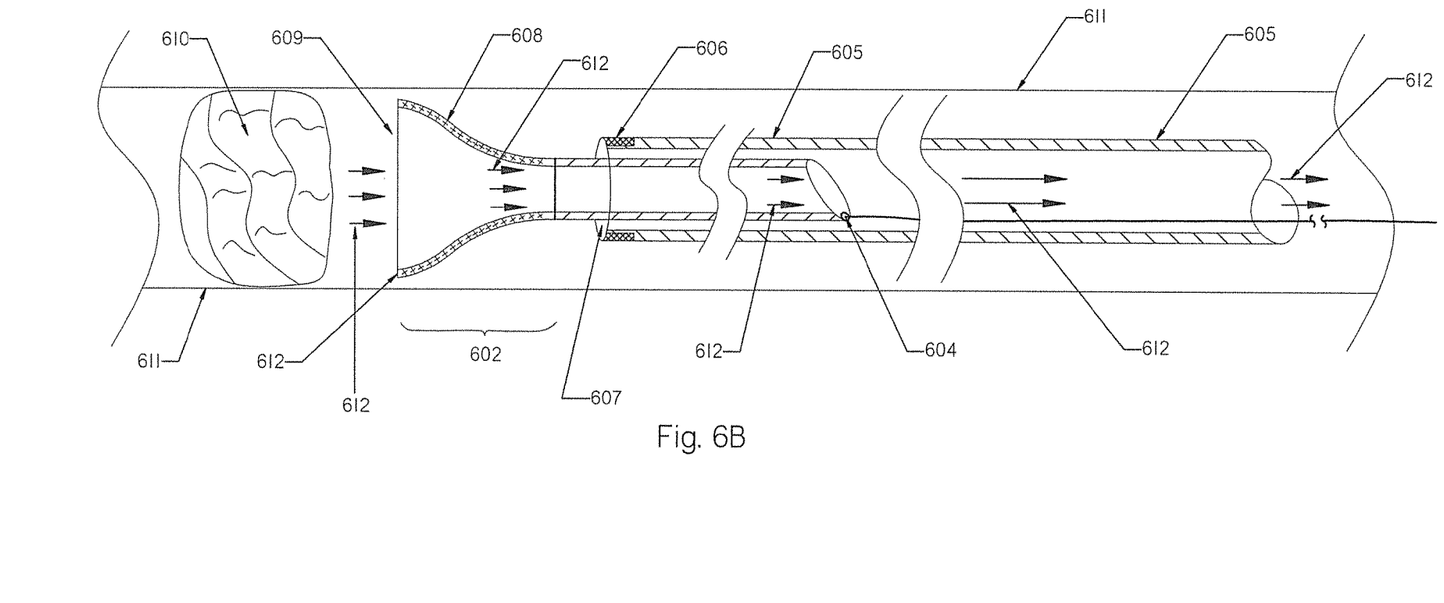
FIG. 6B shows the distal end of the tubular member of FIG. 6A with the expandable tip expanded and positioned adjacent blood clots that are to be removed.

FIG. 6B shows the extension catheter 600 as in FIG. 6A but partially outside the distal end 607 of the guiding catheter 605. The expandable tip 602 is in the expanded configuration and has an enlarged distal aperture 609. The distal aperture 609 of the expandable tip 602 is positioned at clots 610 to be removed from the vessel 611. Upon activation of aspiration at the proximal end of the guiding catheter 605 (not shown), suction of clots 610 begins inside the aperture 609 and along the extension catheter 600 and the guide catheter 605.

Once suction of the clots 610 starts, vacuum pressure shown by arrows 612 increases inside the extension catheter 600 and the guiding catheter 605. Suction activation will cause the soft tip 606 of the guiding catheter 605 to encircle the outer surface of the extension catheter 600, and create a seal.

The distal expandable tip 602 opens to a larger inner lumen 609 than its normal lumen size upon release from the guide catheter 605 when inside the guiding catheter 605. The tubular member 601 with a larger lumen 609 of the expandable tip 602 will increase the efficacy of clot removal.

The tubular member 601 of the extension catheter 600 is configured to be pushed through and out of the guide catheter 605, and retrieved back into the guide catheter 605 using the pushing wire 603, before blood clot removal, during blood clot removal, after clot removal and during removal at combinations of these times.

The expandable tip 602 having a tubular braid and coated with silicone is suitable to assume a pre-set expanded shape of any desired conical configuration when pushed outside of the guide catheter 605.

The extension catheter with an expandable tip that is made of a tubular braid and coated with silicone may be embodied in other forms and configurations without departing from the spirit of the present invention. Furthermore, the embodiments of the expandable tip illustrated in the present invention should be considered in all aspects as illustrative and not restrictive and such expandable tip may also be implemented in a conventional catheter and micro-catheter for any suitable use to treat endovascular and outside of endovascular diseases, illnesses or disorders.

Braided and coiled shafts (also known as braid and coil reinforced shafts) have been a trending topic in the world of medical catheters recently. With the growing popularity of complex minimally invasive surgeries and the rising demands of the procedural requirements, the need for shafts with tighter tolerances and improved characteristics has increased drastically. By utilizing braiding and coiling reinforcements, shafts can be provided with thinner walls while also improving the pushability, steerability, torque, and non-kinking features that non-reinforced shafts lack. With all approaches to tighten the wall of the catheters, a new challenge with catheter compression has arisen and needs to be resolved. More specifically, when the catheter is pushed percutaneously from outside the body to remote locations within the body, often times more than 100 cm from the distal end of the catheter, it often causes a very distal portion of the catheter to compress or create an "accordion" which limits the catheter aspiration and other performance abilities. To address this challenge, a new catheter wall structure is proposed.

Figure 8:
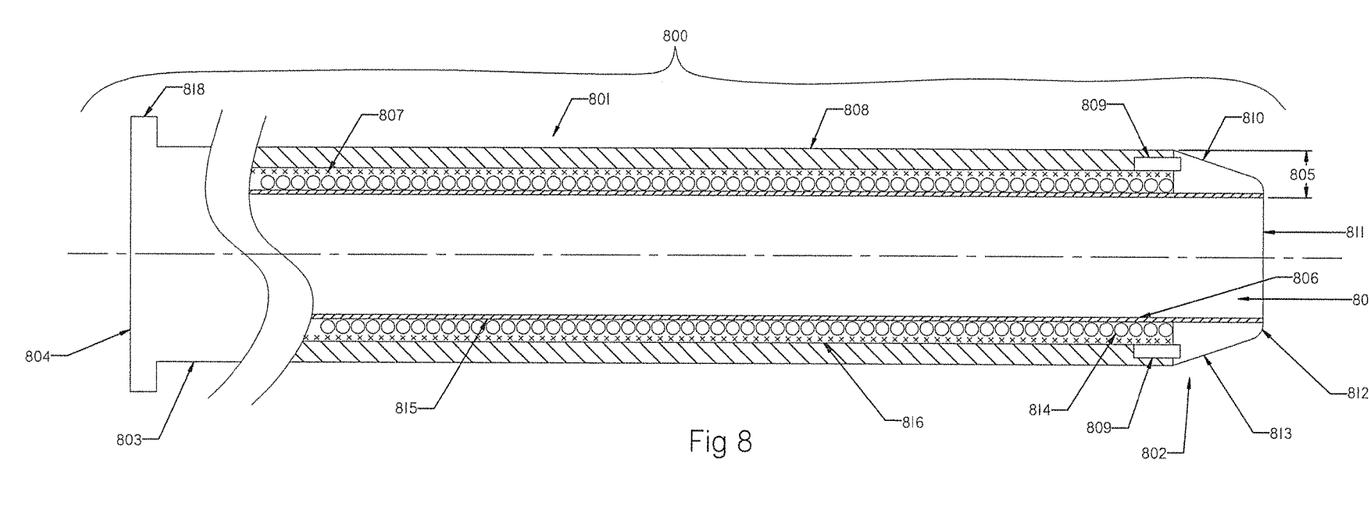
FIG. 8 shows a cross section of an endovascular catheter having a hybrid reinforcement with a braid surrounding a helical coil.

FIG. 8 shows a cross section of an endovascular catheter 800. The catheter 800 has an elongate flexible catheter body 801 having a distal end 802, a proximal end 803, an inner central lumen 804 extending longitudinally through the catheter body 801, and a catheter wall 805. The catheter wall 805 comprises a tubular inner liner 806, a hybrid reinforcement 807 and a variable durometer outer jacket 808, positioned in this order radially from the central lumen 804 to the exterior. A radiopaque marker 809 is located at the proximity of the distal end 802, and a soft tip 810 is located at the very distal end 802 of the catheter 800.

The distal tip 810 of the catheter body 801 is configured to be relatively atraumatic when it engages with tissue (e.g., vascular walls) of the patient, yet stiff enough to allow at least the distal opening 811 to substantially maintain its cross-sectional shape, or otherwise resist geometric deformation as the distal tip is maneuvered over a guidewire or another device (e.g., another catheter). The outer jacket 808 of the catheter 800 defines an angled outer surface 813 that tapers very distally from a diameter of the outer jacket 808 to a smaller outer diameter 812 at the distal end 802 of the catheter 800. The angled outer surface 813 of the tip 810 is often referred to as a soft tip, and helps to guide the distal tip 810 of catheter body 800 along a curved vascular wall and may help reduce adverse interactions between the distal tip 810 of catheter body 800 and the vascular wall.

The radiopaque marker 809 is at least partially embedded in the outer jacket 808 and adhered to the distal end 814 of the hybrid reinforcement 807. This arrangement prevents the distal end 814 of the hybrid reinforcement from being exposed outside the outer jacket 808. The radiopaque marker 809 may be bonded to the distal end 814 of the hybrid reinforcement 807 and/or fused or heat shrunk to the inner liner 806. The radiopaque marker 809 may be formed from any suitable material, and may be in the form of a continuous ring, a discontinuous ring, or multiple segments that extend around the perimeter of the catheter body 801. The radiopaque marker 809 is positioned to indicate the location of the distal tip 810 of the catheter body 801 and is located at the proximity of the distal opening 811.

The inner tubular liner 806 may be formed by dip coating on a removable mandrel or may be in the form of a tubular liner made of PTFE. Optionally, a tie layer surrounding the inner layer 806 (not shown) may be added to provide a better bond when heat shrinking or bonding layers of the catheter wall 805. The tie layer may be made of polyurethane and have a wall thickness of no more than about 0.004 inches, and may extend along at least 3 cm or more from the distal end 809 of the catheter body 801.

The inner liner 806 may be comprised of two or more longitudinal segments (not shown). The first distal segment of the inner liner 806 may be made of PTFE to provide distal inner lubricity, while at least one proximally adjacent segment may be made of, but is not limited to, urethane or polyurethane elastomer or other polymers, to increase the stiffness of the proximal portion of the catheter 800. The length of the distal segment of the inner liner 806 may be 1-25 inches, and the length of the proximally adjacent segment of the inner liner 806 may have a length of 1-80 inches. Alternatively, the inner liner 806 may be terminated before the distal end of the catheter 800 to improve the flexibility of the distal end of the catheter 800. The inner liner 806 may be made of, but is not limited to, urethane, polyurethane or other similar materials. The length of the distal segment of the inner liner 806 may be between 5-50 cm, and preferably 10-20 cm.

The hybrid reinforcement 807 comprises a helical coil 815 and a braid 816 overlying each other. The helical coil 815 surrounds the inner liner 806 when viewed radially from the inner liner 806 towards the outer jacket 808. The braid 816 encircles or overlaps the helical coil 815. The helical coil 815 may be made or formed from a stainless steel or a shape memory alloy (SMA) wire, rounded or flat, with a constant or variable pitch and the desired diameters, and include a tapered configuration if needed. The layout of the helical coil 815 may be adjusted to achieve the desired pitch profile (e.g., the change in pitch over the length). The SMA is an alloy that "remembers" its original shape and when deformed returns to its pre-deformed shape when heated. The SMA preferably comprises an Austenite state at body temperature.

The braid 816 may be formed from a plurality of wire strands having a dimension that is between about 0.0003 inches and about 0.010 inches, and made of one of the following materials: metals, alloys, shape memory material (e.g., Nitinol), cobalt-chromium alloys, Platinum, Platinum-Iridium alloys, polymers (e.g., Nylon, Polyester, etc.), or any combination thereof. The braid 816 may include strands of the same dimensions or of different dimensions that are braided using a circular wire, oval wire, flat wire or any other suitable wire configuration.

The configurations for the hybrid reinforcement 807 may include any desirable structure made of both its components (coil and braid). For example, the configurations for the helical coil 815 may include variable pitch, variable wire size, different outside diameter dimensions, or tapered configuration. The braid 816 may be made in any desirable configuration as listed in the paragraph above. Alternatively, the hybrid reinforcement may have the same structure along the entire length of the catheter 800 with the same helical coil configuration and the same braid.

FIG. 8 shows the hybrid reinforcement 807 comprising the helical coil 815 surrounding the inner liner 806 and the braid 816 surrounding the helical coil 815. Alternatively, the structure of the hybrid reinforcement 807 may be reversed with the braid 816 surrounding the inner liner 806 and the helical coil 815 surrounding the braid 816 (not shown)

The distal end of the coil 815 and the distal end of the braid 816 may be covered by the distal marker 809. The distal end of the coil 815 may be terminated more distally than the overlapping braid or more proximally than overlapping braid (not shown).

Alternatively, the hybrid reinforcement 807 may comprise a braid surrounding the inner layer, and a helical coil surrounding the braid (not shown). The braid may be terminated more distally than the overlapping coil or more proximally than the overlapping coil (not shown).

The structure of the catheter 800, especially the construction of the hybrid reinforcement 807, provides all needed catheter performance characteristics, such as: strength, flexibility, kink resistance, torque, shape retention, and compression resistance. The structure also provides a good integrity of the overall catheter 800 with the overall catheter 800 having a tensile strength higher than 2 lbs., as well as a true 1:1 push/pull while tracking through tortuous anatomy. It is also important to maintain a large inner diameter defined by the catheter wall thickness ratio: the inner diameter to the outer diameter of the catheter 800. It is desirable that the catheter wall thickness ratio is 0.80 or higher.

Figure 9:
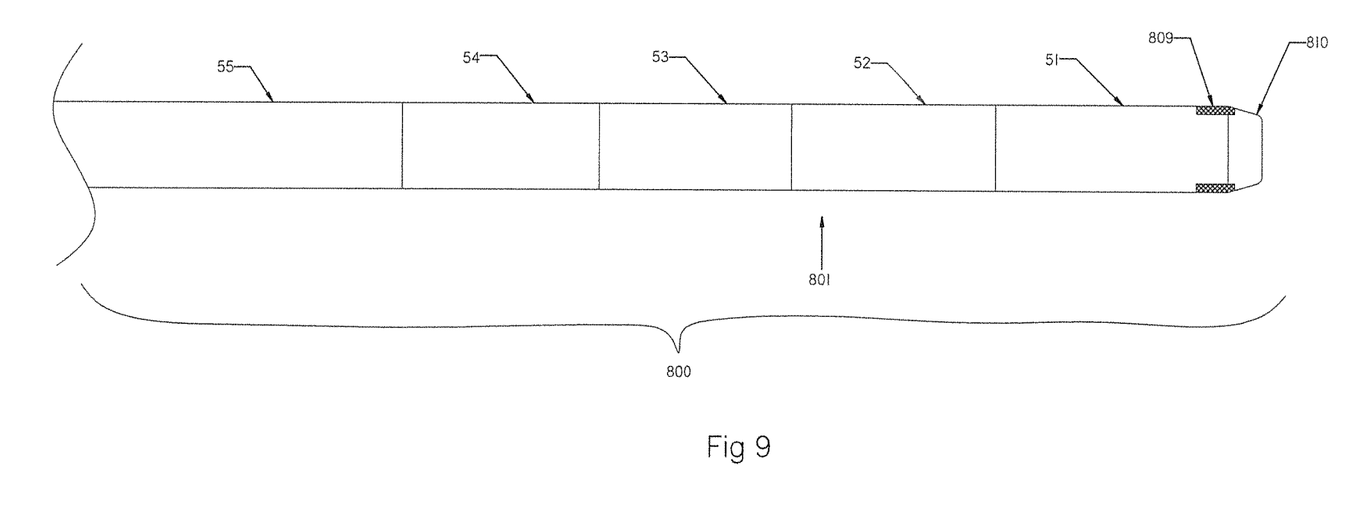
FIG. 9 illustrates the outer jacket of the catheter body.

FIG. 9 illustrates the outer jacket 808 of the catheter body 801. While the outer jacket 808 may be formed of multiple segments, the catheter 800 shown in FIG. 9 is made of five discrete tubular segments, as an example. The segment 51 is the most flexible and may be made from Pebax 2533, among other possible materials. The other segments 52, 53 and 54 are all preferably made from Pebax 3533, although other materials are also possible. The segment 55 is also preferably made from Pebax 6533 or 7533, although other materials are also possible. The outer jacket may be formed from at least two, and as many as twenty or more, discrete tubular segments. The difference in durometer between the tubular segments may be at least about 5 D. The durometer difference between the very proximal and the very distal tubular segments may be at least about 30 D.

The outer jacket 808 is made of polymers with several segments of a variable durometer, with a lower durometer segment usually located on the distal end and higher durometer segments located progressively proximally along the catheter length. The segments of variable flexibility may be made from, but are not limited to, the following materials: Tecoflex EG-80A; Tecoflex EG-85A; Pebax 2533, Pebax 3533, Pebax MX1205; Pebax5533, Pebax 6433; Pebax 7233, Nylon 6, Nylon 12 and any combination thereof.

For increasing the tension resistance in the distal zone of the catheter 800, a support filament may be carried between the inner liner 806 and the hybrid reinforcement 807, or within the helical coil 815 and the braid 816 (not shown). The axially extending filament may increase the tensile strength of the catheter 800 to at least three or more pounds. The filament material may include, but is not limited to, Vectren, Dacron or Kevlar fibers.

Figure 10:
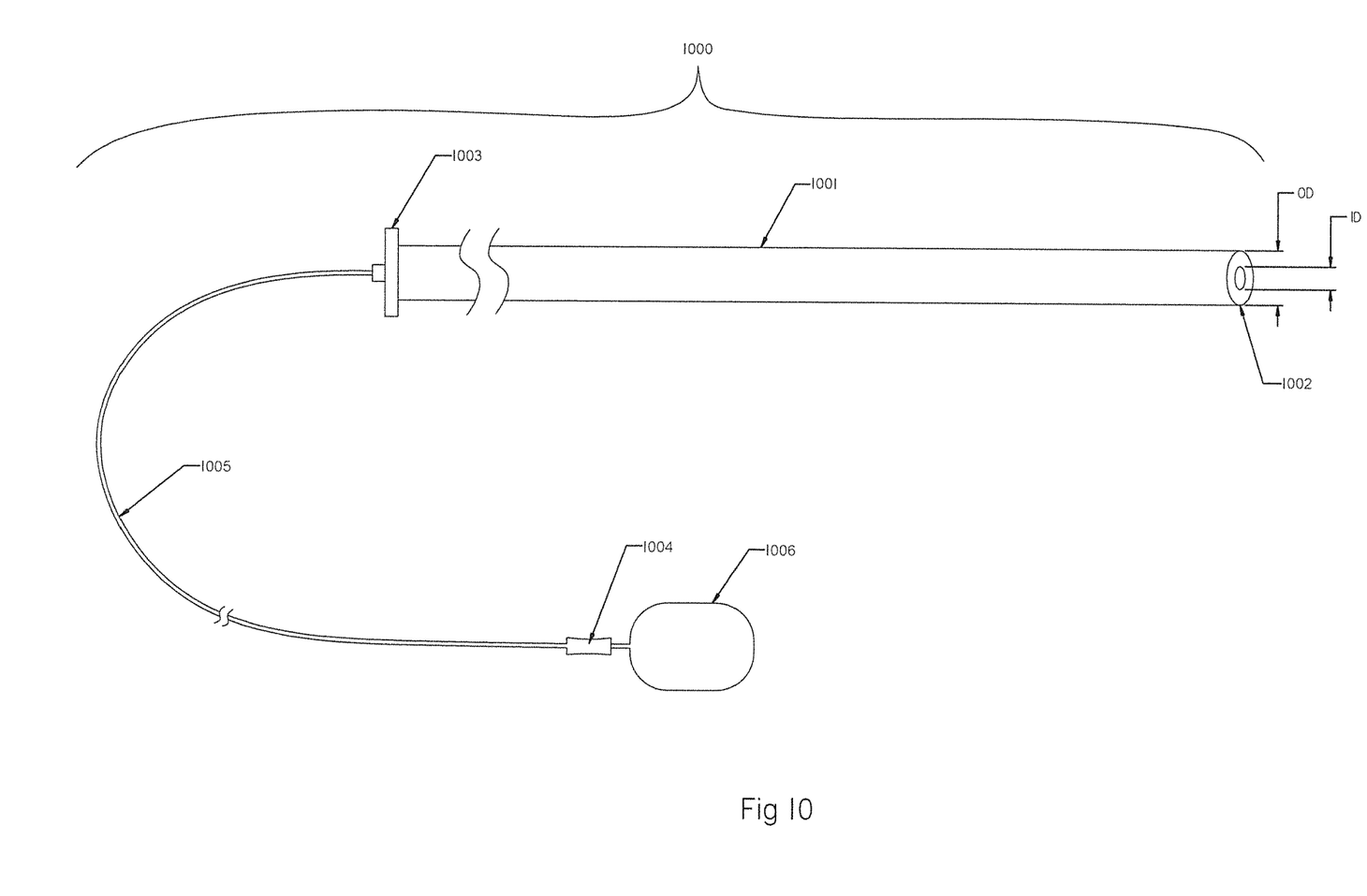
FIG. 10 shows a device for removing blood clots.

FIG. 10 shows another aspect of the present invention, where a device 1000 includes an aspiration catheter 1001 having a distal end 1002 and a proximal end 1003; and a liquid aspiration pump 1004 attached via a tube 1005 to the proximal end 1003 of the aspiration catheter 1001. The liquid aspiration pump 1004 is attached to the blood collecting bag 1006. The liquid aspiration pump 1004 functions to directly remove blood clots and other tissue from the body, unlike commonly-used air aspiration pumps that use air suction from inside the blood container to aspirate clots and other tissue. Cycling of the liquid aspiration pump 1004 may further enhance efficacy to remove clots. Higher clot recanalization rates may be achieved by cyclic aspiration at 3-10 Hz, which in experimental work has outperformed static aspiration when liquid medium is used to aspirate clots.

To secure maximum clot removal efficacy, the aspiration catheter 1001 should have the largest inner diameter and a thin wall to be compliant with the limiting inner diameters of introducer sheaths and guiding catheters that are commonly used in the most interventional procedures. However, to secure catheter performance characteristics and compatibility with introducer sheaths and guiding catheter, it is advantageous that the ratio R of the catheter inner lumen diameter ID to the catheter outer lumen diameter OD should be more than 0.80.

The liquid aspiration pump 1004 has mechanically actuated positive displacement powered by a rotating motor incorporated in the pump assembly (not shown) and may be powered by line power or battery. It is desirable to cycle the rotating motor at less than 10 Hz frequency while maintaining the motor speed below 2000 RPM to achieve the best efficacy to remove clots and other liquids. Cycling of the liquid aspiration pump 1004 will cause the pump aspiration pressure to continuously change up and down, and produce a pulsating effect on blood clots to be removed. Such blood clot pulsation will disrupt or break the structure of blood clots and prevent the aspiration catheter 1001 from clogging. The logic behind this approach is that cycling pressure/forces will induce fatigue on the blood clots or other tissue to be removed, thereby enabling the removal of more entrenched blood clots and prevent catheter clogging.

Although this invention has been described with reference to preferred embodiments and examples, those having ordinary skill in this art will recognize that changes may be made in form and detail without departing from the spirit and scope of the invention as found in the claims which follow.

What is claimed is:

1. An endovascular catheter comprising:
   an elongate catheter body having a proximal end, a distal end and a central lumen extending longitudinally through the catheter body, wherein the catheter body comprises a catheter wall that has an inner liner, a hybrid reinforcement, a distal tip and a variable durometer outer jacket,
   wherein the hybrid reinforcement comprises a helical coil and a braid that encircles the helical coil, and a radiopaque marker positioned on the distal end of the catheter body about the outer circumference of the hybrid reinforcement,
   wherein the distal end of the helical coil and the distal end of the braid are terminated between distal and proximal ends of the radiopaque marker located on the distal end, and wherein the inner liner is at least partially made of PTFE.

2. The catheter of claim 1, wherein the distal tip is extended beyond the radiopaque marker.

3. The catheter of claim 1, wherein a tie layer surrounds the inner liner.

4. The catheter of claim 1, wherein the radiopaque marker is at least partially embedded in the outer jacket.

5. The catheter of claim 1, wherein the radiopaque marker is configured as a continuous ring.

6. The catheter of claim 1, wherein a support filament is carried between the inner liner and the hybrid reinforcement.

7. The catheter of claim 1, wherein a support filament is carried inside the hybrid reinforcement, between the helical coil and the braid.

8. The catheter of claim 1, wherein the distal tip tapers distally.

9. The catheter of claim 1, wherein the catheter has an inner diameter and an outer diameter, and wherein a thickness ratio of the inner diameter to the outer diameter is 0.80 or higher.

10. The catheter of claim 1, wherein a tensile strength of the catheter is higher than 2 lbs.

11. The catheter of claim 1, wherein the hybrid reinforcement is made of one of the following materials: metals, alloys, shape memory alloys, polymers, or a combination thereof.

12. The catheter of claim 1, wherein the outer jacket has a distal end, and is made of polymers having a plurality of segments of variable durometer, with a lower durometer segment located on the distal end and higher durometer segments located progressively proximally along the catheter length.

13. An endovascular catheter comprising:
    an elongate catheter body having a proximal end, a distal end and a central lumen extending longitudinally through the catheter body, wherein the catheter body comprises a catheter wall that has an inner liner, a hybrid reinforcement, a distal tip, and a variable durometer outer jacket,
    wherein the hybrid reinforcement comprises a helical coil and a braid that encircles the helical coil, and a radiopaque marker positioned on the distal end of the catheter body about the outer circumference of the hybrid reinforcement,
    wherein the distal end of the helical coil and the distal end of the braid are terminated between distal and proximal ends of the radiopaque marker, and
    wherein the structure of the hybrid reinforcement is the same along the entire length of the catheter body.

14. An endovascular catheter comprising:
    an elongate catheter body having a proximal end, a distal end and a central lumen extending longitudinally through the catheter body, wherein the catheter body comprises a catheter wall that has an inner liner, a hybrid reinforcement, a distal tip, and a variable durometer outer jacket with a lower durometer segment located on the distal end,
    wherein the hybrid reinforcement comprises a helical coil and a braid that encircles the helical coil, and a radiopaque marker positioned on the distal end of the catheter body about the outer circumference of the hybrid reinforcement, and
    wherein the distal end of the helical coil and the distal end of the braid are terminated between distal and proximal ends of the radiopaque marker.

* * * * *